(12) United States Patent
Zanfei et al.

(10) Patent No.: US 10,006,895 B2
(45) Date of Patent: Jun. 26, 2018

(54) SYSTEM AND METHOD FOR MONITORING ATMOSPHERIC POLLUTION

(71) Applicant: C.R.D. CENTRO RICERCHE DUCATI TRENTO S.R.L., Rovereto (IT)

(72) Inventors: Adriano Zanfei, Rovereto (IT); Christian Marzadro, Rovereto (IT); Ernesto Miorando, Rovereto (IT)

(73) Assignee: C.R.D. CENTRO RICERCHE DUCATI TRENTO S.R.L., Roverto (TN) (IT)

( * ) Notice: Subject to any disclaimer, the term of this patent is extended or adjusted under 35 U.S.C. 154(b) by 490 days.

(21) Appl. No.: 14/429,023

(22) PCT Filed: Sep. 20, 2013

(86) PCT No.: PCT/IB2013/002062
§ 371 (c)(1),
(2) Date: Mar. 18, 2015

(87) PCT Pub. No.: WO2014/068376
PCT Pub. Date: May 8, 2014

(65) Prior Publication Data
US 2015/0253300 A1 Sep. 10, 2015

(30) Foreign Application Priority Data
Sep. 20, 2012 (IT) .............................. MO2012A0222

(51) Int. Cl.
*G01N 7/00* (2006.01)
*G01N 33/00* (2006.01)
*G01N 1/02* (2006.01)

(52) U.S. Cl.
CPC ... *G01N 33/0075* (2013.01); *B60W 2550/402* (2013.01); *B60W 2550/404* (2013.01); *B60Y 2200/13* (2013.01); *G01N 2001/021* (2013.01)

(58) Field of Classification Search
USPC ..................... 73/23.2, 23.31, 114.69, 114.71
See application file for complete search history.

(56) References Cited

U.S. PATENT DOCUMENTS

| 4,121,548 A | 10/1978 | Hattori et al. |
| 5,105,651 A * | 4/1992 | Gutmann ................ F01N 11/00 73/23.31 |

(Continued)

FOREIGN PATENT DOCUMENTS

| EP | 1 113 268 A1 | 7/2001 |
| EP | 1 505 385 A1 | 2/2005 |

(Continued)

OTHER PUBLICATIONS

International Search Report, dated Feb. 21, 2013, from corresponding PCT application.

*Primary Examiner* — Lam Nguyen
(74) *Attorney, Agent, or Firm* — Young & Thompson

(57) ABSTRACT

A system for monitoring atmospheric pollution, includes a mobile appliance fitted on a vehicle and a remote processing unit, the mobile appliance including a location unit for detecting geographic coordinates of the vehicle, an atmospheric sensor for detecting an atmospheric pollution value, a transmission unit for transmitting the geographic coordinates and the atmospheric pollution value, the remote processing unit including a receiving unit for receiving the geographic coordinates and the atmospheric pollution value, a processing unit for processing the geographic coordinates and the atmospheric pollution value for monitoring the atmospheric pollution inside a geographic area. The system further includes: a verification sensor; comparison elements (Continued)

between the atmospheric pollution value and a reference pollution value detected by the verification sensor, substantially in correspondence to the same geographic coordinates; signalling elements operatively associated with the comparison elements for signalling the need for a calibration of the atmospheric sensor of the mobile appliance.

18 Claims, 3 Drawing Sheets

(56) References Cited

U.S. PATENT DOCUMENTS

| | | | | |
|---|---|---|---|---|
| 6,176,125 | B1 * | 1/2001 | Hirano | G01F 1/704 |
| | | | | 73/114.69 |
| 7,251,981 | B2 * | 8/2007 | Sasaki | G01N 27/16 |
| | | | | 73/23.21 |
| 2005/0088299 | A1 | 4/2005 | Bandy et al. | |
| 2011/0163892 | A1 | 7/2011 | Groves et al. | |

FOREIGN PATENT DOCUMENTS

| | | |
|---|---|---|
| WO | 95/34076 A1 | 12/1995 |
| WO | 2001/069136 A2 | 6/2011 |

* cited by examiner

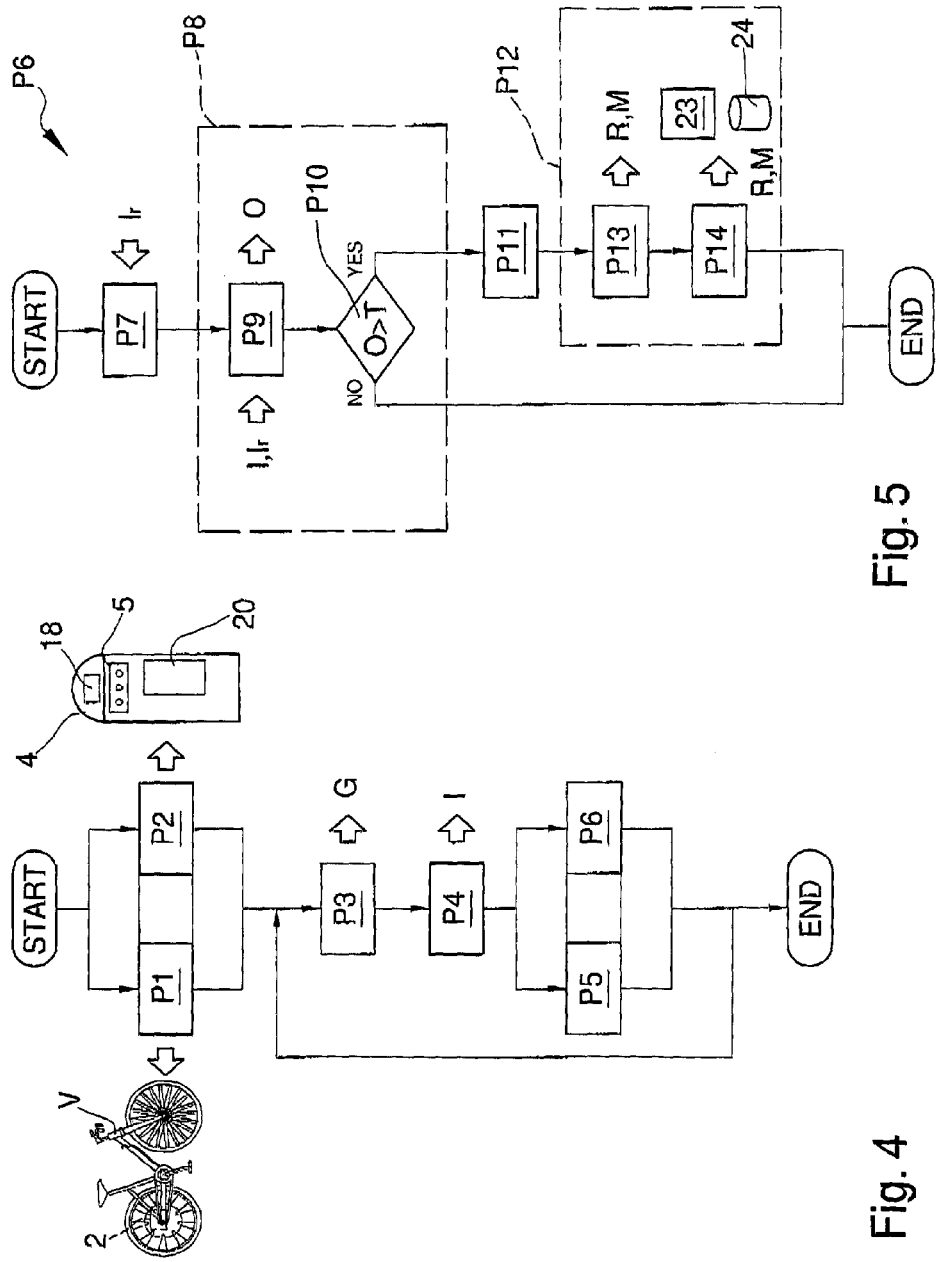

SYSTEM AND METHOD FOR MONITORING ATMOSPHERIC POLLUTION

TECHNICAL FIELD

The present invention relates to a system and a method for monitoring atmospheric pollution.

BACKGROUND ART

The need is increasingly more felt to monitor and reduce atmospheric pollution which, as is known, is the cause of numerous and by now widespread illnesses affecting mankind such as, for example, cardio-circulatory lung diseases and immune system illnesses.

To monitor atmospheric pollution, in particular, the use is known of special detection units, suitably located inside a geographic area to be monitored and having atmospheric sensors able to detect gases and polluting substances such as, e.g., carbon monoxide (CO), nitrogen oxides ($NO_x$), sulphur oxides ($SO_x$), hydrocarbons ($C_xH_y$), ozone ($O_3$) and particulate (PTS).

Nevertheless, such units are fixed installations and, consequently, they permit detecting atmospheric pollution values only in correspondence to precise sites inside the geographic area to be monitored, while the atmospheric pollution in correspondence to other areas must necessarily be determined by approximation.

The use is also known of mobile laboratories having several atmospheric sensors and the equipment needed to process and analyze data.

Nevertheless, the use of such mobile laboratories is very expensive, inasmuch as it requires the use of complex equipment and the continuous on-board presence of qualified personnel.

Furthermore, by means of the use of mobile laboratories, an in any case small number of detection operations can be performed, and with checks repeated inside the same area greatly dilated in time.

To overcome the above drawbacks affecting known solutions, electronic appliances are used installable on vehicles, having one or more atmospheric sensors and suitable communication devices, able to send the collected pollution data to one or more remote processing units.

In particular, the document EP 1 113 268 A1 describes a method and an appliance for monitoring the quality of air inside a predetermined geographic area, wherein the appliance comprises a fixed station and at least a mobile station installed on a vehicle.

The mobile station has atmospheric sensors for detecting polluting gases, a satellite receiver to determine the position of the vehicle over time, an acquisition unit which receives data from the atmospheric sensors and from the satellite receiver and a transmission interface able to transmit the collected data.

The fixed station, furthermore, comprises a processor with communication device of the modem type with antenna and a software program for the display and analysis of the data collected by and received from the mobile station.

Such known method and appliance propose to provide a continuous control of the pollution conditions inside the monitored area by means of a representation of average concentrations (hourly, daily, monthly, etc.) of the polluting substances present.

Furthermore, the document WO 2011/069136 A2 describes an electric wheel for bicycles which can be provided with at least an environmental sensor, a satellite receiver for determining the position of the bicycle over time, and a communication unit for transmitting the detected data relating to the environmental pollution and to the position.

However, the appliances of known type are not free from drawbacks.

In fact, commonly used environmental sensors require continuous maintenance jobs that have to be repeated over time and which aim at setting and calibrating the metrological characteristics defining the precision of the sensors themselves, such as e.g., accuracy, resolution, zero drift and span drift.

In particular, the precision of an environmental sensor is the degree of approximation with which the sensor is able to define the measured quantity, accuracy is the capacity of the sensor to detect a concentration value of a gas more or less close to the real concentration value, while resolution is the smallest quantity the sensor is able to detect.

Furthermore, fundamental parameters in assessing the efficacy of an environmental sensor are the zero drift, which indicates the gradual variance in time of the average response to a zero-setting gas, i.e., to a gas that should be detected as zero by the sensor, and the span drift, which instead indicates the gradual variance in time of the average response to a gas of known concentration.

These parameters can vary over time and this inevitably ends up negatively affecting the quality of the measurements taken by the atmospheric sensor.

The periodical intervention of skilled technicians is therefore required to make calibrations and this operation often requires the de-installation of the sensor and its dispatch to laboratories able to perform all the fine-tuning operations. Inevitably, this involves high maintenance costs, as well as periods of inactivity of the atmospheric sensors which are not at all negligible and are repeated over time.

DESCRIPTION OF THE INVENTION

The main aim of the present invention is to provide a system and a method for monitoring atmospheric pollution which allow effectively and quickly performing the calibration of the atmospheric sensors used.

Another object of the present invention is to provide a system and a method for monitoring atmospheric pollution which permit cutting maintenance costs of the atmospheric sensors used.

Another object of the present invention is to provide a system and a method for monitoring atmospheric pollution which permits eliminating or in any case considerably reducing the down times of the atmospheric sensors used.

Another object of the present invention is to provide a system and a method for monitoring atmospheric pollution which allow overcoming the mentioned drawbacks of the state of the art within the ambit of a simple, rational, easy, effective to use and low cost solution.

The above objects are achieved by the present system for monitoring atmospheric pollution, according to claim 1.

The above objects are also achieved by the present method for monitoring atmospheric pollution, according to claim 12.

BRIEF DESCRIPTION OF THE DRAWINGS

Other characteristics and advantages of the present invention will become more evident from the description of a preferred, but not sole, embodiment of a system and a method for monitoring atmospheric pollution, illustrated purely as an example but not limited to the annexed drawings in which:

FIGS. 4 and 5 are general bloc diagrams which illustrate the method according to the invention.

EMBODIMENTS OF THE INVENTION

Figure 1:
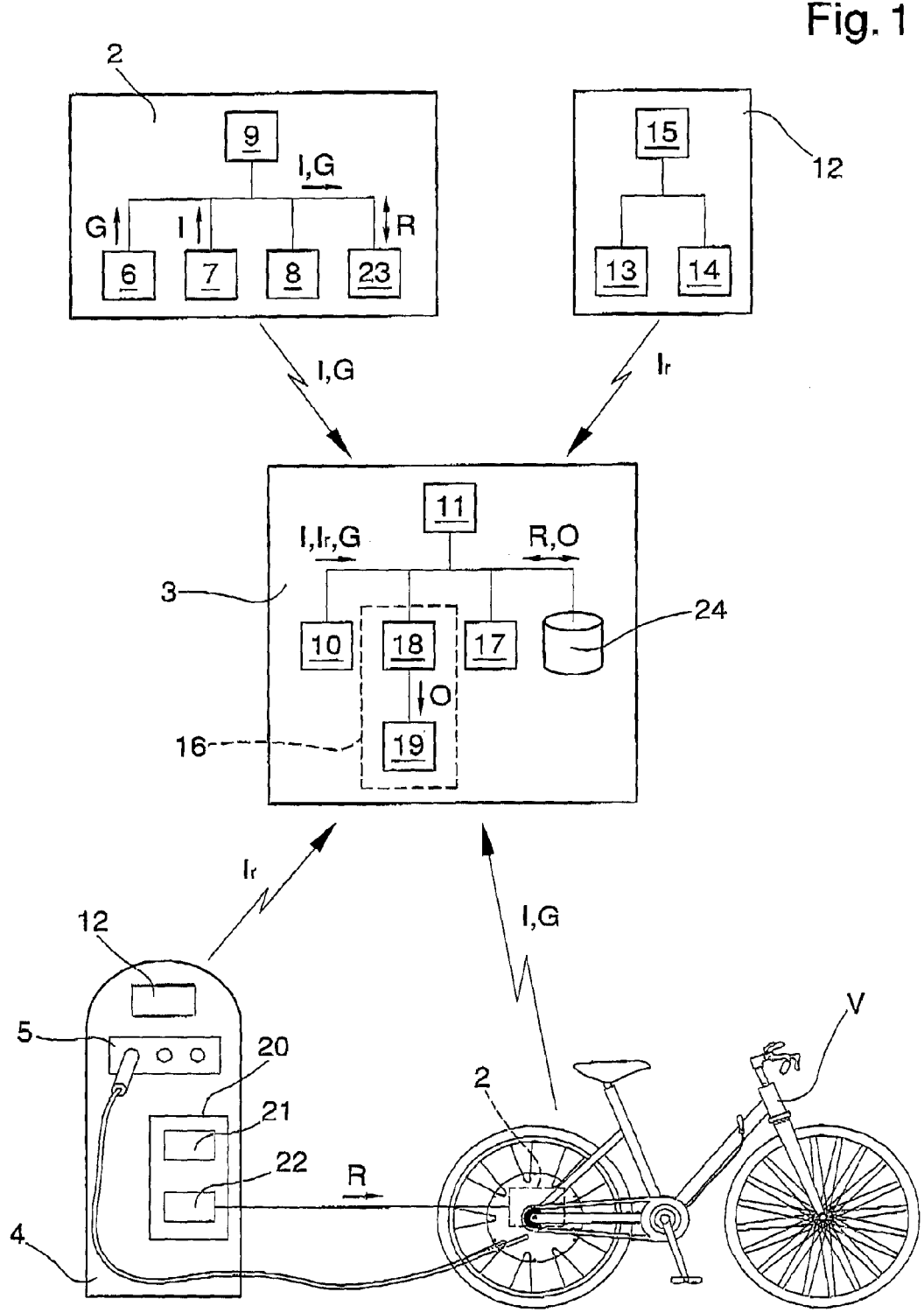
FIG. 1 is a general functional diagram which illustrates the system according to the invention.

With particular reference to such figures, globally indicated by 1 is a system for monitoring atmospheric pollution.

In particular, the system 1 comprises a plurality of mobile appliances 2 which can be fitted on respective vehicles V.

System 1 also comprises at least a remote processing unit 3 suitable for communicating with each of the mobile appliances 2.

According to a preferred embodiment of the system 1, the mobile appliances 2 can be installed on electric vehicles of different types, such as electric cars and trucks, motor-driven bikes, electric scooters and similar vehicles, and the system 1 comprises one or more recharging columns 4 located inside a determinate geographic area and provided with recharging means 5 for the electric recharge of the battery of the vehicle V.

In a preferred embodiment, the mobile appliances 2 can be installed on pedal assisted electric bikes.

Each mobile appliance 2 comprises a location unit 6 suitable for detecting the geographic coordinates G of the vehicle V and made up, e.g., of a satellite signal receiver.

Each mobile appliance 2 also comprises at least an atmospheric sensor 7 suitable for detecting at least an atmospheric pollution value I in the proximity of the vehicle V.

Preferably, each mobile appliance 2 comprises several atmospheric sensors selected from:
 a carbon monoxide (CO) sensor;
 a nitrogen oxide ($NO_x$) sensor;
 a sulphur oxide ($SO_x$) sensor;
 a hydrocarbon ($C_xH_y$) sensor;
 an ozone ($O_3$) sensor;
 a temperature sensor;
 a humidity sensor.

In particular, to effectively measure atmospheric pollution, it is preferable to combine the use of at least one sensor for measuring the level of a polluting gas with a sensor for measuring the temperature and/or the humidity of the environment.

The use cannot however be ruled out of atmospheric sensors of a different type. It is also pointed out that, by the expression "atmospheric pollution value" is meant one or more values, measurable by means of such atmospheric sensors 7, relating to the physical quantities suitable for indicating the concentration of physical, chemical and biological polluting agents in the air, such as, e.g., carbon monoxide (CO), nitrogen oxides ($NO_x$), sulphur oxides ($SO_x$), hydrocarbons ($C_xH_y$), ozone ($O_3$) and particulate (PTS), as well as all those further physical quantities suitable for determining the atmospheric conditions in the proximity of the vehicle such as, e.g., air temperature and humidity.

Each mobile appliance 2 also comprises a transmission unit 8 suitable for transmitting the geographic coordinates G and the atmospheric pollution value I to the remote processing unit 3.

For example, the transmission unit 8 can consist of a radio-wave transmitter device suitable for transmitting through the conventional mobile phone network or of a similar device.

Each mobile appliance 2 also comprises processing means 9, consisting e.g. of a micro controller or of a similar device, operatively connected to the location unit 6, to the atmospheric sensor 7 and to the transmission unit 8.

The remote processing unit 3 comprises a receiving unit 10 suitable for receiving the geographic coordinates G and the atmospheric pollution value I transmitted by the transmission units 8 of each of the mobile appliances 2.

For example, the receiving unit 10 can consist of a radio-wave receiver device suitable for receiving through the conventional mobile phone network or of a similar device.

The remote processing unit 3 also comprises at least a processing unit 11 suitable for processing all the received information and relating to the different atmospheric pollution values I detected in correspondence to different geographic coordinates G, in order to monitor the conditions of atmospheric pollution inside one or more geographic areas.

Usefully, the remote processing unit 3 can comprise several processing units 11 consisting, e.g., of one or more electronic processors operatively connected to one another by means of the conventional Internet network and having one or more dedicated software applications.

Advantageously, with reference to a preferred embodiment, shown in FIG. 1, the system 1 comprises several fixed appliances 12, arranged in correspondence to predefined geographic coordinates G and comprising one or more verification sensors 13.

In particular, the fixed appliances 12 can consist of conventional fixed units located inside the geographic area to be monitored and commonly used to monitor the atmospheric pollution.

Usefully, as shown in FIG. 1, one or more fixed appliances 12 can be implemented inside the recharging columns 4 for electrically recharging the vehicles V.

Each fixed appliance 12 also comprises a transmission unit 14 suitable for transmitting reference pollution values $I_r$ to the receiving unit 10 of the remote processing unit 3.

For example, the transmission unit 14 can consist of a radio wave transmission device suitable for transmitting through the conventional mobile phone network or of a similar device.

Each fixed appliance 12 also comprises processing means 15, consisting e.g. of a micro controller or of a similar device, operatively connected to the verification sensor 13 and to the transmission unit 14.

The remote processing unit 3 has suitable comparison means 16 able to compare the atmospheric pollution values I detected by means of the atmospheric sensors 7 with respective reference pollution values $I_r$ detected by the verification sensors 13, in correspondence to or in any case in the proximity of the same geographic coordinates G.

The remote processing unit 3 also comprises signalling means 17, operatively connected to the comparison means 16, and suitable for signalling the need for a calibration operation on one of the atmospheric sensors 7, in the event of the atmospheric pollution value I detected by such atmospheric sensor differing in a substantial way from the reference pollution value $I_r$ detected by at least one of the verification sensors 13 in correspondence to the same geographic coordinates G.

With reference to a preferred embodiment of the system 1, shown schematically in FIG. 1, the comparison means 16 and the signalling means 17 are made by means of one or more software applications and/or one or more hardware components implemented on the remote processing unit 3.

Different embodiments of the system 1 cannot however be ruled out wherein the comparison means 16 and the signalling means 17 are implemented on different electronic appliances, e.g., on the same mobile appliances 2 installed on board the vehicles V.

The use of the verification sensors 13, together with the comparison means 16 and the signalling means 17, permits checking in real time the effectiveness and reliability of the atmospheric sensors 7 and the actual correctness of the measurements taken of the atmospheric pollution values I.

This way, therefore, it is possible to quickly and simply identify all those atmospheric sensors 7 requiring a calibration operation, thus avoiding pointless tests or periodical calibration operations on all the atmospheric sensors 7.

This therefore permits considerably reducing the total number of calibration operations and the overall time of inactivity of the single atmospheric sensors 7 and instead permits carrying out only targeted jobs only on the atmospheric sensors 7 which really need calibrating.

This way, when a vehicle V having a mobile appliance 2 transits in correspondence to, or in the proximity of, one of the fixed appliances 12, the comparison means 16 make a comparison between the atmospheric pollution value I detected by the atmospheric sensor of the mobile appliance 2 and the reference pollution value $I_r$ detected by the verification sensor 13 of the fixed appliance 12, therefore checking whether or not it is necessary to perform a calibration operation on the atmospheric sensor 7.

In particular, the comparison means 16 comprise calculation means 18 of one or more offset values O, calculated as the difference between the atmospheric pollution values I and the reference pollution values $I_r$ in correspondence to the same geographic coordinates G and to a predefined time instant.

The comparison means 16 also comprise comparing means 19 suitable for comparing each calculated offset value O with at least a predefined threshold value T.

If the module of the calculated offset value O is bigger than the threshold value T, then the signalling means 17 signal the need for a maintenance job on the relative atmospheric sensor 7.

The calculation means 18 and the comparing means 19 can be made, e.g., by means of one or more applications or software components and/or one or more hardware components or devices implemented on the remote processing unit 3.

Different embodiments of the system 1 cannot however be ruled out wherein the calculation means 18 and the comparing means 19 are implemented on different electronic appliances, e.g., on the same mobile appliances 2 installed on board the vehicles V.

Figure 2:
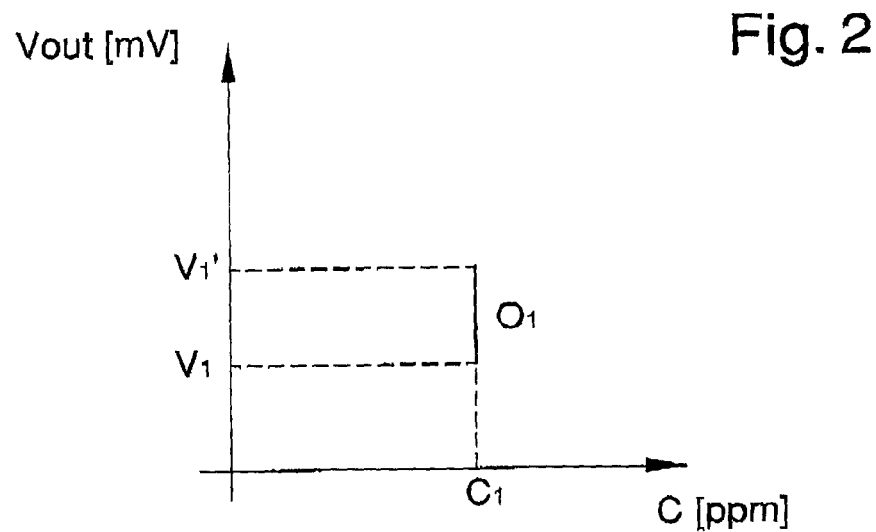
FIGS. 2 and 3 are graphs, given by way of example, that compare possible output signals of an atmospheric sensor and of a verification sensor, respectively, of the system according to the invention, measured according to the changes in concentration of a polluting gas.
Figure 3:
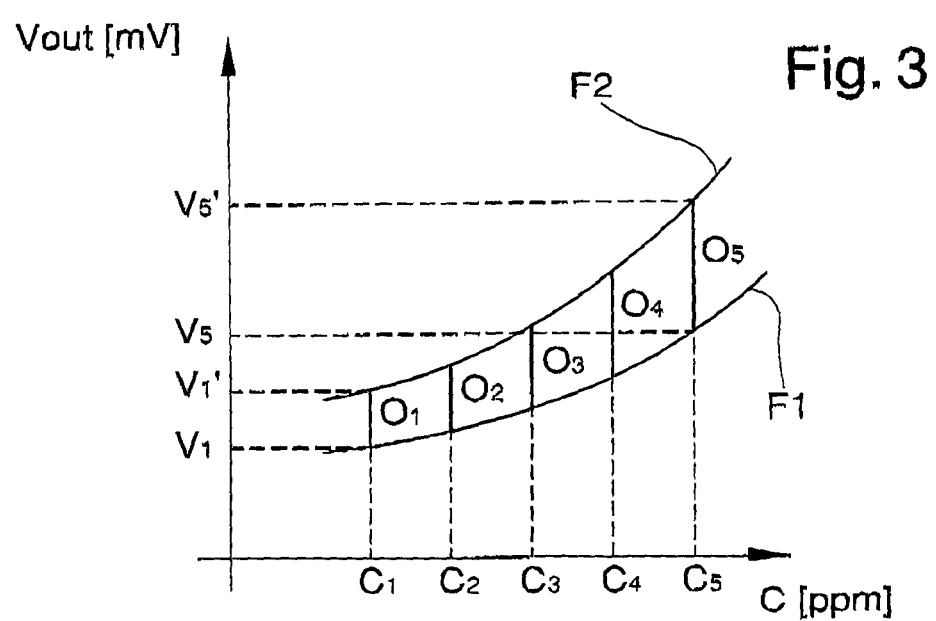

By way of example only, the FIGS. 2 and 3 show possible output signal values, of an atmospheric sensor 7 and of a verification sensor 13, respectively, of the system 1, according to the changes in concentration C of a polluting gas.

The graphs shown in such illustrations indicate, in abscissa, the concentration C of a generic polluting gas expressed in parts per million and, in ordinate, the output voltage $V_{out}$ of a generic atmospheric sensor expressed in mV.

In particular, in FIG. 2 by reference $V_1$ is indicated a possible output voltage value of a verification sensor 13, while by reference $V_1'$ is indicated a possible output voltage value of an atmospheric sensor 7 of one of the mobile appliances 2. Both the output voltage values $V_1$ and $V_1'$ correspond to a concentration value C of a polluting gas detected in a specific moment and in correspondence to determinate geographic coordinates G inside the geographic area to be monitored.

The offset value $O_1$ is calculated as the difference between the output voltage $V_1'$ of the atmospheric sensor 7 and the output voltage $V_1$ of the verification sensor 13.

The FIG. 3 shows a first curve F1 and a second curve F2 illustrating a possible characteristic voltage-concentration of a verification sensor 13 installed on a fixed appliance 12 and a possible characteristic voltage-concentration of an atmospheric sensor 7 installed on a mobile appliance 2 respectively.

In correspondence to a specific gas concentration value, e.g. in correspondence to the concentration value $C_1$, the verification sensor 13 produces an output voltage $V_1$, while the atmospheric sensor 7 produces an output voltage $V_1'$. For such concentration value $C_1$, the offset value $O_1$ is calculated as the difference between the output voltage V: and the output voltage $V_1$.

In the same way, in correspondence to different concentration values $C_1$, $C_2$, $C_3$, $C_4$ and $C_5$, the verification sensor 13 produces relative output voltages $V_1$, $V_2$, $V_3$, $V_4$ and $V_5$, while the atmospheric sensor 7 produces output voltages $V_1'$, $V_2'$, $V_3'$, $V_4'$ and $V_5'$. For such concentration values $C_1$, $C_2$, $C_3$, $C_4$ and $C_5$, respective offset values $O_1$, $O_2$, $O_3$, $O_4$ and $O_5$ can be calculated as the difference between the output voltages $V_1'$, $V_2'$, $V_3'$, $V_4'$ and $V_5'$ and the output voltages $V_1$, $V_2$, $V_3$, $V_4$ and $V_5$.

Alternatively or also together with the use of the reference pollution values $I_r$ detected by the fixed appliances 12, it is possible to compare the atmospheric pollution value I detected by an atmospheric sensor 7 on a mobile appliance 2 with the atmospheric pollution values I detected by the atmospheric sensors 7 of other mobile appliances 2 present in correspondence to or in any case in the proximity of the same geographic coordinates G at a specific moment or time interval.

In this case, the verification sensors consist of the atmospheric sensors 7 of the other mobile appliances 2 present in correspondence to a predefined time instant and in correspondence to or in any case in the proximity of the same geographic coordinates G and the offset value O can be calculated, for example, as the difference between the atmospheric pollution value I of the atmospheric sensor 7 to be tested and the median of the atmospheric pollution values I detected by the other atmospheric sensors 7.

Advantageously, the system 1 comprises an automatic calibration unit 20 operatively connectable to each of the mobile appliances 2 and suitable for performing the automatic calibration of one or more adjusting parameters R of each of the atmospheric sensors 7, so that the pollution value detected by said atmospheric sensor 7 substantially corresponds to the reference pollution value $I_r$ detected by the verification sensor 13.

This way, the atmospheric sensors 7 can be calibrated in a fully automatic way, without the need for intervention by skilled personnel.

This therefore involves a considerable reduction in the total maintenance time of the system 1, as well as a considerable reduction in the inactivity time of the atmospheric sensors 7 used.

In particular, each automatic calibration unit 20 comprises processing means 21, consisting e.g. of a micro controller, and connection means 22 connectable to a mobile appliance 2.

The connection means 22 can consist, e.g., of a special connection port for cable connection or of a short-range radio-wave transmission/receiving device, of the type of a Bluetooth, Wi-Fi device or the like.

Advantageously, with reference to a preferred embodiment, the system 1 comprises a plurality of automatic calibration units 20 made integral with the recharging columns 4.

This way, the automatic calibration can be made of the atmospheric sensor 7 of one of the mobile appliances 2 when the relative electric vehicle V is connected to the recharging means 5 of the recharging column 4.

Usefully, if the recharging column 4 is equipped with the fixed appliance 12 and therefore with at least a verification sensor 13, then it is possible to perform both the control and, if necessary, the automatic calibration of the atmospheric sensor 7 of a mobile appliance 2 when the relative electric vehicle V is connected to the recharging column 4.

In particular, with reference to a preferred but not exclusive embodiment of the system 1 shown in FIG. 1, one of the adjusting parameters R modifiable by means of the automatic calibration unit 20 can consist of a conversion coefficient R applicable to the output voltage value $V_{out}$ of the atmospheric sensor 7 to be calibrated to obtain the atmospheric pollution value I detected.

For example, such conversion coefficient R can consist of a multiplier coefficient applicable by means of the following formula:

$$I = R * V_{out}.$$

This way, by changing the value of a conversion coefficient R of the atmospheric sensor 7 to be calibrated, it is possible to adjust the atmospheric pollution value I detected by the atmospheric sensor itself according to the calculated offset value O.

In particular, the value of the conversion coefficient R can be adjusted so the atmospheric pollution value I detected by the atmospheric sensor 7 in correspondence to determinate geographic coordinates G corresponds to the reference pollution value $I_r$ detected by the verification sensor 13.

Usefully, the system 1 can envisage the use of at least a conversion matrix M, wherein are shown all the conversion coefficients R split up by each atmospheric sensor 7 and by different concentration values C.

Several conversion matrices M can be stored and used for different types of polluting gases.

Usefully, the system 1 comprises storage means suitable for storing the conversion coefficients R of each of the atmospheric sensors 7 and, if necessary, the offset values O and the conversion matrices M.

In particular, the storage means can comprise a rewritable memory 23 present on each of the mobile appliances 2 and suitable for storing one or more conversion coefficients R of one or more atmospheric sensors 7 present on the mobile appliance itself.

Alternatively, or together with the use of local rewritable memories 23 present on the mobile appliances 2, the storage means can comprise one or more mass memories 24 or the like present in the remote processing unit 3 and suitable for storing the conversion coefficients R of all the atmospheric sensors 7.

Usefully, one of the adjusting parameters R modifiable by means of the automatic calibration unit 20 can consist of a variable electrical physical quantity of one or more electronic components of the atmospheric sensor 7 to be calibrated.

For example, such variable electrical physical quantity can consist of the resistance value of a variable load resistor of the atmospheric sensor 7.

This way, by varying the resistance value of the variable resistor and/or of another electronic component of the atmospheric sensor 7, the output voltage $V_{out}$ of the atmospheric sensor itself can be adjusted according to the calculated offset value O.

In particular, with reference for example to the FIG. 2, the resistance value can be regulated so the output voltage $V_1'$ of the atmospheric sensor 7 corresponds to the output voltage $V_1$ of the verification sensor 13.

The method according to the invention is described below and schematically illustrated in the FIGS. 4 and 5.

The method according to the invention first of all envisages the installation of a plurality of mobile appliances 2 on respective electric vehicles V (step P1) and the installation of a plurality of fixed appliances 12 in correspondence to predetermined geographic coordinates G, inside a geographic area to be monitored (step P2).

The method therefore envisages the following steps:
  detecting the geographic coordinates G of each vehicle V by means of the respective location units 6 (step P3);
  detecting the atmospheric pollution value I by means of the atmospheric sensors 7 of the mobile appliances 2 (step P4);
  processing the geographic coordinates G and the detected atmospheric pollution values $I_r$ for monitoring the atmospheric pollution inside one or more geographic areas to be monitored (step P5).

Advantageously, at the same time as the monitoring of the atmospheric pollution (step P5) or periodically, the method envisages the verification of the measurements made by means of the atmospheric sensors 7 (step P6).

As detailed in FIG. 5, such check envisages the reading of reference pollution values $I_r$ detected by verification sensors 13 (step P7) and the comparison of the atmospheric pollution values I detected with the reference pollution values $I_r$ detected in the proximity of the same geographic coordinates G (step P8).

In particular, for each of the atmospheric sensors 7, the comparison of the detected atmospheric pollution value I with the reference pollution value $I_r$ envisages:
  the calculation of an offset value O as difference between the atmospheric pollution value I and the reference pollution value $I_r$, in correspondence to a predefined time instant (step P9);
  the comparison of the calculated offset value O with at least a predefined threshold value T (step P10).

For all those atmospheric pollution values I which differ substantially from the reference pollution value $I_r$, the signalling means 17 signal the need for a calibration operation of the relative atmospheric sensor 7 (step P11).

In particular, the need to perform a calibration operation on the atmospheric sensor 7 is signalled if the module of said offset value O is higher than such threshold value.

The method can also include the storage of the calculated offset values O.

If necessary, the reference pollution value $I_r$ can be calculated as the median of the atmospheric pollution values I detected by a plurality of atmospheric sensors 7, substantially in correspondence to the same geographic coordinates and to at least a predefined time instant.

Advantageously, the method envisages the automatic calibration of at least an adjusting parameter R of the atmospheric sensor 7 (step P12).

In particular, with reference to a preferred but not exclusive embodiment, the automatic calibration can envisage the change of a conversion coefficient R applicable to the output voltage value $V_{out}$ of the atmospheric sensor 7 to be calibrated to obtain the detected atmospheric pollution value I (step P13).

For example, such conversion coefficient R can consist of a multiplier coefficient applicable by means of the following formula:

$$I = P * V_{out}$$

This way, by changing the value of a conversion coefficient R of the atmospheric sensor 7 to be calibrated, the atmospheric pollution value I detected by the atmospheric sensor itself can be adjusted according to the calculated offset value O.

In particular, the value of the conversion coefficient R can be adjusted so the atmospheric pollution value I detected by the atmospheric sensor 7 in correspondence to determinate geographic coordinates G corresponds to the reference pollution value $I_r$ detected by the verification sensor 13.

Usefully, the method can envisage the use of at least a conversion matrix M, wherein are shown all the conversion coefficients R split up by each atmospheric sensor 7 and by different concentration values C.

Several conversion matrices M can be stored and used for different types of polluting gases.

Usefully, the method envisages the storage of the conversion coefficients R of each of the atmospheric sensors 7 and, if necessary, of the conversion matrices M (step P14).

Usefully, the automatic calibration can envisage the change of a variable electrical physical quantity of one or more of the electronic components of the atmospheric sensor 7 to be calibrated.

For example, such variable electrical physical quantity can consist of the resistance value of a variable load resistor of the atmospheric sensor 7.

This way, by varying the resistance value of the variable resistor and/or of another electronic component of the atmospheric sensor 7, the output voltage $V_{out}$ of the atmospheric sensor itself can be adjusted according to the calculated offset value O.

In particular, with reference for example to the FIG. 2, the value of the resistance can be adjusted so the output voltage $V_1'$ of the atmospheric sensor 7 corresponds to the output voltage $V_1$ of the verification sensor 13.

Advantageously, the step P2 of the method can comprise the preparation of the automatic calibration units 20 directly on the recharging columns 4.

The atmospheric sensors 7 are automatically calibrated by the automatic calibration unit 20 when the electric vehicle V is connected to a recharging column 4.

The invention claimed is:

1. System (1) for monitoring atmospheric pollution, comprising at least a mobile appliance (2) fitted on a vehicle (V) and at least a remote processing unit (3), wherein said mobile appliance (2) comprises:
    at least a location unit (6) suitable for detecting geographic coordinates (G) of said vehicle (V);
    at least an atmospheric sensor (7) suitable for detecting at least an atmospheric pollution value (I);
    at least a transmission unit (8) suitable for transmitting said geographic coordinates (G) and said atmospheric pollution value (I);
and wherein said remote processing unit (3) comprises:
    at least a receiving unit (10) suitable for receiving said geographic coordinates (G) and said atmospheric pollution value (I);
    at least a processing unit (11) suitable for processing said geographic coordinates (G) and said atmospheric pollution value (I) for monitoring the atmospheric pollution inside at least one geographic area;
wherein said system (1) comprises:
    at least a verification sensor (7, 13);
    comparison means (16) between said atmospheric pollution value (I) and at least a reference pollution value ($I_r$) detected by said verification sensor (7, 13), substantially in correspondence to the same geographic coordinates (G);
    signalling means (17) operatively associated with said comparison means (16) and suitable for signalling the need for a calibration of said atmospheric sensor (7) of the mobile appliance (2), if said atmospheric pollution value (I) substantially differs from said reference pollution value ($I_r$),
wherein said system (1) comprises at least an automatic calibration unit (20) operatively connectable to said mobile appliance (2) and suitable for automatically calibrating at least an adjusting parameter (R) of said atmospheric sensor (7) of the mobile appliance (2), so that said atmospheric pollution value (I) detected by the atmospheric sensor (7) substantially corresponds to said reference pollution value ($I_r$) detected by the verification sensor (7, 13), and wherein:
    said mobile appliance (2) is fitted onto an electric vehicle (V),
    said system (1) comprises at least a recharging column (4) with electric recharging means (5) of said electric vehicle (V) and said automatic calibration unit (20) is associated with said recharging column (4) and is suitable for automatically calibrating said atmospheric sensor (7) when said electric vehicle (V) is connected to said electric recharging means (5).

2. System (1) according to claim 1, wherein said system (1) comprises at least a fixed appliance (12) fitted in correspondence to predetermined geographic coordinates (G) and having said verification sensor (13).

3. System (1) according to claim 1, wherein said system (1) comprises a plurality of said mobile appliances (2) fitted on different vehicles (V) and by the fact that said at least one verification sensor (7) is made up of at least an atmospheric sensor (7) of said mobile appliances (2).

4. System (1) according to claim 3, wherein said system (1) comprises a plurality of verification sensors (7) made up of said atmospheric sensors of respective mobile appliances (2), and by the fact that said comparison means (16) comprise determination means of said reference pollution value (Ir), determined as the median of the pollution values detected by said verification sensors (7), substantially in correspondence to the same geographic coordinates (G) and to at least a predefined time instant.

5. System (1) according to claim 1, wherein said comparison means (16) comprise calculation means (18) of at least an offset value (0), calculated as the difference between said atmospheric pollution value (I) and said reference pollution value ($I_r$), substantially in correspondence to the same geographic coordinates (G) and to at least a predefined time instant.

6. System (1) according to claim 5, wherein said comparison means (16) comprise comparing means (19) of said offset value (O) with at least a predefined threshold value (T), said signalling means (17) being suitable for signalling the need for a calibration of said atmospheric sensor (7) if the module of said offset value (O) is bigger than said threshold value (T).

7. System (1) according to claim 5, wherein said system (1) comprises storage means (23, 24) of said conversion coefficient (R).

8. System (1) according to claim 1, wherein said adjusting parameter (R) comprises at least a conversion coefficient (R) suitable for obtaining said atmospheric pollution value (I) starting from at least an output electric signal ($V_{out}$) of said atmospheric sensor (7).

9. System (1) according to claim 8, wherein said system (1) comprises storage means (23, 24) of said offset value (O).

10. System (1) according to claim 1, wherein said adjusting parameter (R) comprises at least a variable electric physical quantity of at least one of the electronic components of said atmospheric sensor (7).

11. Method for monitoring the atmospheric pollution, comprising the following steps:
fitting at least one atmospheric sensor (7) onto at least a vehicle (V);
detecting the geographic coordinates (G) of said vehicle (V);
detecting the atmospheric pollution value (I) by means of said atmospheric sensor (7);
processing said geographic coordinates (G) and said atmospheric pollution value (I) for monitoring the atmospheric pollution inside at least one geographic area;
wherein said method comprises the following steps:
comparing the detected atmospheric pollution value (I) with at least a reference pollution value ($I_r$) detected by at least a verification sensor (7, 13), substantially in correspondence to the same geographic coordinates (G);
if said pollution value substantially differs from said reference pollution value ($I_r$), then signalling the need for a calibration of said atmospheric sensor (7),
wherein, following said step of signalling, said method comprises the step of automatically calibrating at least an adjusting parameter (R) of said atmospheric sensor (7), and wherein:
said vehicle (V) is an electric vehicle (V),
said method comprises the step of fitting at least a recharging column (4) with electric recharging means (5) of said electric vehicle (V) and
said step of automatically calibrating the atmospheric sensor (7) is performed when said electric vehicle (V) is connected to said electric recharging means (5).

12. Method according to claim 11, wherein said method comprises fitting at least a fixed appliance (12) with said verification sensor (13) in correspondence to predetermined geographic coordinates (G).

13. Method according to claim 11, wherein said method comprises fitting a plurality of said atmospheric sensors (7) onto different vehicles (V) and by the fact that at least one verification sensor (7) is made up of at least one of said atmospheric sensors (7).

14. Method according to claim 13, wherein said step of comparing comprises at least a step of determining said reference pollution value ($I_r$) as the median of the atmospheric pollution values (I) detected by said verification sensors (7), substantially in correspondence to the same geographic coordinates (G) and in correspondence to at least a predefined time instant.

15. Method according to claim 11, wherein said step of comparing comprises calculating at least an offset value (O) as the difference between said atmospheric pollution value (I) and said reference pollution value ($I_r$) in correspondence to at least a predefined time instant.

16. Method according to claim 15, wherein said step of comparing comprises comparing said offset value (O) with at least a predefined threshold value (T) and by the fact that said step of signalling the need for a calibration of said atmospheric sensor (7) is performed if the module of said offset value (O) is bigger than said threshold value (T).

17. Method according to claim 11, wherein said adjusting parameter (R) comprises at least a conversion coefficient (R) suitable for obtaining said pollution value starting from at least an output electric signal ($V_{out}$) of said atmospheric sensor (7).

18. Method according to claim 11, wherein said adjusting parameter (R) comprises at least a variable electric physical quantity of at least one of the electronic components of said atmospheric sensor (7).

\* \* \* \* \*